United States Patent [19]
Barbee et al.

[11] Patent Number: 5,381,234
[45] Date of Patent: Jan. 10, 1995

[54] METHOD AND APPARATUS FOR REAL-TIME FILM SURFACE DETECTION FOR LARGE AREA WAFERS

[75] Inventors: Steven G. Barbee, Dover Plains; Tony F. Heinz, Chappaque, both of N.Y.; Richard J. Lebel, Sheldon, Vt.; Leping Li, Poughkeepsie; Victor J. Silvestri, Hopewell Junction, both of N.Y.

[73] Assignee: International Business Machines Corporation, Armonk, N.Y.

[21] Appl. No.: 173,390

[22] Filed: Dec. 23, 1993

[51] Int. Cl.$^6$ .............................................. G01J 4/00
[52] U.S. Cl. .................................. 356/369; 356/244; 250/225
[58] Field of Search ................. 250/225; 356/364, 365, 356/366, 367, 369, 370, 244

[56] References Cited
U.S. PATENT DOCUMENTS

| | | | |
|---|---|---|---|
| 3,542,482 | 11/1970 | Wilks, Jr. | 356/244 |
| 3,704,955 | 12/1972 | Siegler, Jr. | 356/244 |
| 5,185,644 | 2/1993 | Shimoyama et al. | 250/225 |

FOREIGN PATENT DOCUMENTS

| 1124723 | 5/1989 | Japan | 250/225 |
|---|---|---|---|

*Primary Examiner*—Richard A. Rosenberger
*Assistant Examiner*—Jason D. Eisenberg
*Attorney, Agent, or Firm*—Whitham, Curtis, Whitham & McGinn

[57] ABSTRACT

A method and apparatus for measuring with monolayer sensitivity in real-time the condition of a sample, includes a device for producing a modulated and collimated, p-polarized excitation light beam, a device for directing the p-polarized beam to a surface of the sample such that an angle of incidence of the p-polarized light beam with respect to the normal of the surface is at the Brewster angle, first and second reflecting devices between which the sample is positioned, a mechanism for adjusting a distance between the first and second reflecting devices to adjust a number of interactions of the p-polarized excitation light beam with the sample surfaces, and a detector for detecting the p-polarized light beam output intensity distribution with respect to frequency front the sample surfaces. The reflecting devices and the sample are adjustably maintained parallel to one another to thereby maintain the Brewster angle of the input excitation light beam with respect to the normal of the sample surface. As a result, loss of light intensity due to reflections at the sample surfaces is minimized, interference or noise can be minimized, and a high signal-to-noise ratio is achieved. With the structure and method of the invention, a real time non-destructive device and method for the detection of species on the sample surface are provided which enable the determination of a critical endpoint with monolayer resolution and the presence (or absence) of impurities detrimental to the process yield in a fabrication process. The obtained real-time information of the surface condition can be used to control the wafer processing control devices, thereby achieving closed-loop wafer process control.

23 Claims, 4 Drawing Sheets

METHOD AND APPARATUS FOR REAL-TIME FILM SURFACE DETECTION FOR LARGE AREA WAFERS

BACKGROUND OF THE INVENTION

1. Field of the Invention

The present invention generally relates to a method and apparatus for inspecting objects and more particularly to a method and apparatus for performing film surface detection (e.g., oxide film etching endpoint detection, film surface contamination detection, etc.) for overlayers on a sample (e.g., a silicon wafer).

2. Description of the Related Art

Fourier-Transform infrared (FTIR) spectroscopy can be used as an extremely sensitive endpoint detection scheme for the etching of thin film overlayers on silicon (e.g., silicon dioxide thin film etching by hydrogen fluoride vapor (HF)). This operation is performed by monitoring the appearance of vibrational features, such as those associated with the hydrogen-passivated silicon surface. In recent tests, a native oxide layer has been removed from the silicon surface by vapor phase HF etching prior to the deposition of tungsten silicide. To obtain an adequate real-time, signal-to-noise ratio, a sample geometry allowing multiple reflections is necessary in which infrared (IR) radiation interacts with the silicon surface a plurality of times. Indeed, for real-time measurement a single pass of the beam through the surface will not be adequate due to the poor signal-to-noise ratio.

Conventionally, the multiple reflections of the IR radiation have been achieved only by using specially prepared or modified silicon substrates in which the infrared radiation is made to propagate within the sample (as compared to propagating externally through the sample). The specially prepared or modified silicon substrates may include bevelled ends which are typically cut at a 45-degree angle at each end, to ensure that the IR radiation beam propagates internally and interacts with the surface a plurality of times before exiting from the other end. The specially prepared or modified silicon substrates are costly and inefficient to produce. Indeed, the specially prepared wafers which are bevelled or cut at a 45-degree angle at each end result in the wafer being typically broken or destroyed and thus the wafer is rendered worthless in terms of further processing. Further, the use of monitor wafers would not be indicative of the surface condition of the product wafers such as the presence of contamination or species left on the surface. These attributes vary from wafer-to-wafer and from lot-to-lot.

Hence, for the foregoing reasons, the geometry of the specially prepared silicon substrates is not transferable to conventional silicon wafers (i.e., absent the special preparations thereof) and indeed precludes using the FTIR spectroscopy as a real-time surface monitoring method for conventional silicon wafers since such wafers are not, as a practical matter, built to have bevelled ends or the like. Further, to build such wafers or modify conventional wafers to have the special geometry is inefficient and adds extra processing steps.

Thus, the conventional arrangement does not support multiple interactions with the surface of conventional silicon wafers, let alone multiple external interactions with the surface. Indeed, such arrangements (e.g., wafers having bevelled or cut ends) do not support external transmission and reflection through the wafer.

Therefore, a problem of the conventional systems is that there is no apparatus and method for performing real-time, nondestructive, in situ measurements of surface properties of a conventional wafer using multiple external transmission and reflection.

SUMMARY OF THE INVENTION

It is therefore an object of the present invention to provide a system and method for detecting and measuring properties of a conventional double-side polished sample (e.g., silicon wafers), which would be advantageous for applications such as establishing the removal of native oxide and full surface passivation before entering the next process step and monitoring possible contamination responsible for delayed, cascaded and very costly adhesion lift-off problems in subsequent processing. The system and method according to the invention allow measurements to be reliably and easily made at any desired point along the processing stream of the wafer.

In a first aspect according to the invention, an apparatus and method have been provided for the detection and monitoring of an object (e.g., a silicon wafer) which has been inserted between first and second reflecting surfaces (e.g., mirrors). A distance between the mirrors is adjustable and multiple interactions of infrared radiation with the wafer surface are obtained using the plurality of high-reflectivity mirrors.

A primary feature of the invention is maintaining the mirrors and the wafer sample parallel to one another and maintaining a Brewster angle of the input beam of p-polarization to the normal of the sample surface to thereby minimize the loss of light intensity due to reflections at the wafer surface.

More specifically, the angle of incidence between a collimated p-polarized beam and the normal to the wafer surface is adjustably set and maintained at the Brewster angle. The importance of maintaining the Brewster angle is that interference-generated noise and the loss of transmitted intensity due to multiple-reflected beams at the silicon surfaces can be minimized (if not entirely prevented), and maximum transmission of the beam can be achieved. Indeed, if the sample surface and the reflecting surfaces were not parallel to one another (and thus the Brewster angle were not maintained) or the incident beam was not collimated, or the incident beam does not have p-polarization, 100% reflection and transmission of the beam could not be achieved and interference and noise would severely degrade the signal-to-noise ratio.

The above feature is made possible by the provision of the plurality (e.g., two) of highly reflecting mirrors having the sample sandwiched therebetween and being adjustable such that the three components (e.g., the wafer surfaces and the two mirrors) are parallel and the incident probe beam is well-collimated as well as p-polarized. In an exemplary embodiment, a holder member for holding the sample includes both reflecting mirrors built therein and holds the wafer by spring-loaded compression screws against pads (e.g., made of Teflon) at the periphery to maintain the wafer parallel to the reflecting mirrors mounted in the holder. This entire assembly can be mechanically aligned by adjusting means (e.g., screw mechanisms, rack and gear mechanisms or the like) to achieve the desired Brewster angle in conjunction with adjustment of the incident beam angle.

Using the present invention, measurements can be routinely and reliably made, in a nondestructive manner, in process line operations on wafers as they progress in the process stream and feedback can be provided in real-time. Further, the structure and method of the invention minimize loss of transmitted intensity due to reflections at wafer surfaces.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1A:
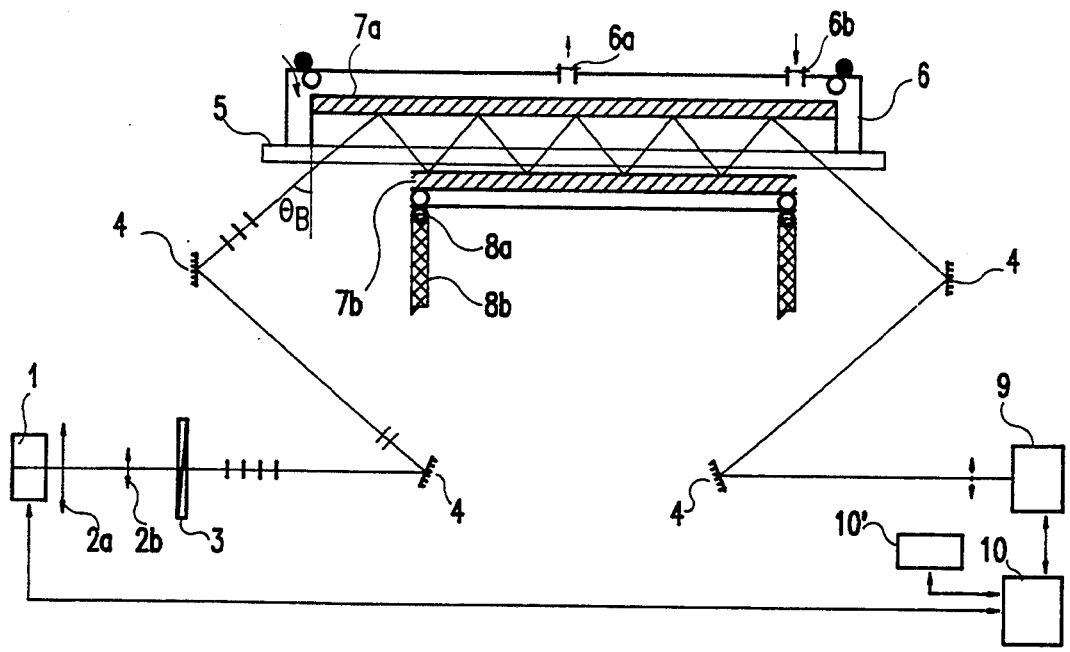
FIG. 1a is an overall plan view of a detection system according to a first embodiment of the invention.

Referring now to the drawings, and more particularly to FIG. 1a, there is shown an overall schematic of the system architecture according to a first embodiment of the invention.

In FIG. 1a, an excitation light beam is provided from a modulated light source 1. Preferably, the light source is an infrared (IR) light source for emitting an IR light beam. However, as is evident, the light source can be a source having any wavelength (e.g., visible, ultraviolet, etc.) so long as it can be modulated and detected for demodulation by Fourier Transformation. Further, the light source can be a laser.

The light beam emitted by the light source is preferably collimated by one or more beam collimating means (e.g., 2a, 2b). The beam collimating means includes one or more collimating lenses such as biconvex lenses or the like.

The collimated light beam is transmitted to a linear polarizer 3 which includes means for passing therethrough p-polarized light only. Preferably, the means for passing p-polarized light includes birefringent materials. It is clear that, while FIG. 1a illustrates the light source, beam collimating means, and linear polarizer as being separate elements, it is recognized that these elements can be easily integrated into a single structure so long as a light beam which is collimated and p-polarized is produced.

Figure 1B:
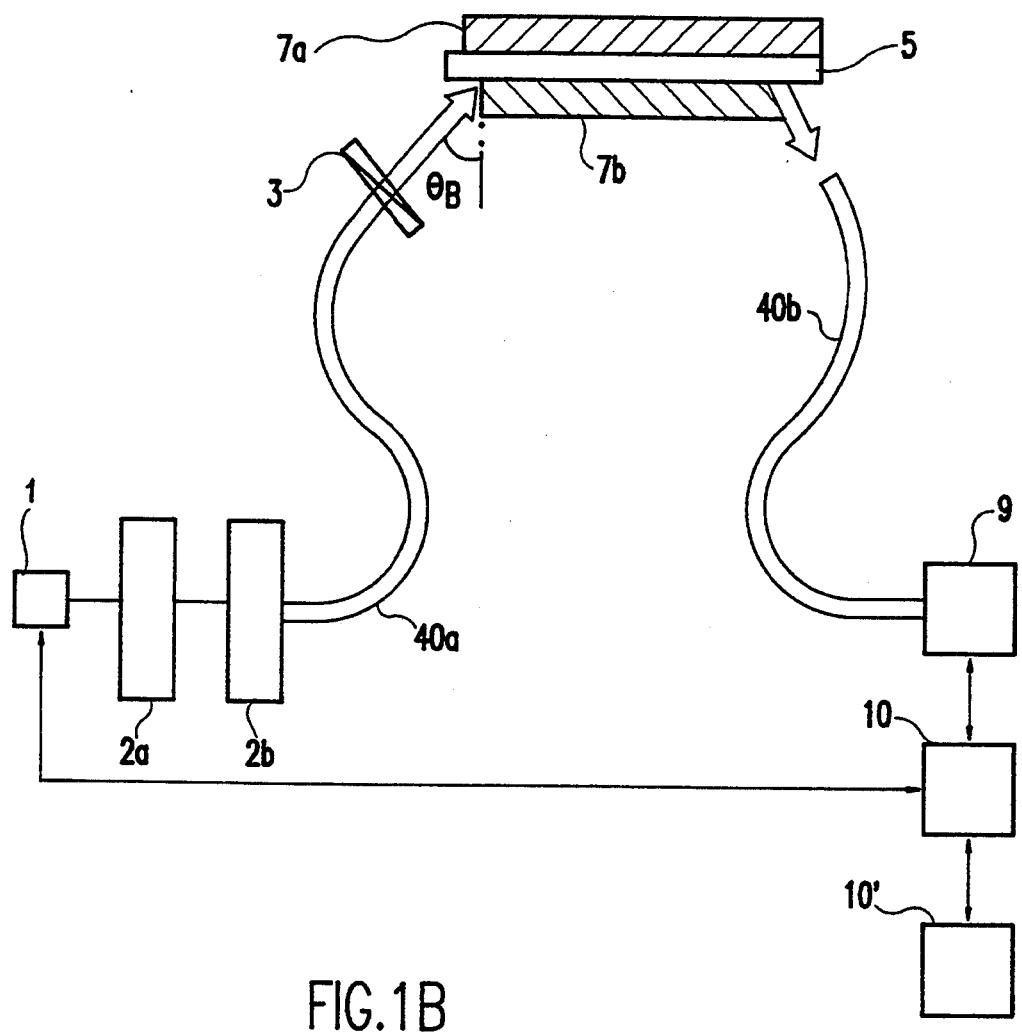
FIG. 1b illustrates a system similar to that of FIG. 1a according to the invention in which optical fibers are utilized in lieu of reflecting means 4.

The p-polarized light is transmitted through the polarizer and may be reflected by reflecting means 4 which may include one or more mirrors. The use of mirrors is advantageous in reducing the amount of space required by the apparatus in that the positioning of the optical path of the light beam can be suitably adjusted (e.g., "folded") to fit space requirements. However, the reflecting means 4 (e.g., the mirrors) does not constitute a critical element of the invention and is not required absent the desire to "fold" the optical path of the beam as discussed above. For example, the mirrors may be replaced by optical fibers or the like to guide the beam so long as the beam remains collimated and p-polarized. FIG. 1b illustrates such an arrangement in which optical fiber 40a is provided between the output of lens 2b and the input to linear polarizer 3. Optical fiber 40b receives the light beam having been multiply reflected by the reflecting mirrors through the sample, and provides the output to the detector 9.

The p-polarized light is reflected by the reflecting means 4 to the surface of a sample 5 (e.g., a silicon wafer or the like), which is substantially transparent to the p-polarized light. Alternatively, the beam may be emitted, collimated, and p-polarized, and then transmitted directly to the sample 5, without the use of any intermediate reflecting means. The sample can be any material (e.g., sapphire, glass, silicon, etc.) which is substantially transparent to a desired wavelength (e.g., IR, visible light, ultraviolet region). The exemplary embodiment of FIG. 1a illustrates a double-polished silicon wafer as the sample 5.

The sample 5 is held by a holder member 6. Preferably, the holder member includes a vacuum chuck which holds the wafer at its periphery. However, any holder member will suffice so long as the wafer is held in a nondestructive/nondisruptive manner. A vacuum chuck is advantageous in terms of the wafer being reliably held and positioned and the holder 6 not damaging the wafer as the wafer is held thereby. The vacuum chuck is coupled to a vacuum source (e.g., means for producing a subatmospheric pressure) and includes a first orifice 6a for connection to a vacuum valve and a second orifice 6b for connection to a vacuum relief valve. The vacuum chuck is preferably made out of "Teflon" (e.g., PTFE) or the like due to its lightweight but durable properties. However, the form and structure of the holder member is not critical to the invention.

A plurality of mirrors (e.g., first and second mirrors 7a, 7b) are provided to ensure reflection and transmission of the collimated p-polarized light beam through the sample 5. The sample 5 is intermediate the mirrors 7a, 7b. As shown in FIG. 1a, the first mirror 7a may be fixedly mounted in the holder member 6 and a second mirror may be mounted externally of the holder member 6 on an adjustable moving means such as a support member 8a on movable rails 8b, which is movable in a direction normal to a surface of the sample being investigated, and which includes adjusting means for adjusting a distance between the first and second mirrors. Preferably, the rails on either end of the second mirror are individually adjustable such that parallelism of the first and second mirrors and sample is achieved and maintained. The sample 5 is inserted between the first and second mirrors in a "sandwich" fashion (e.g., the sample is sandwiched or intermediate the first and second mirrors in a contact or non-contact manner).

Alternatively, the first mirror may be adjustably mounted in the holder member and the second mirror may be mounted on a separate fixed mechanism.

Alternatively, a mechanism may be provided such that both the first and second mirrors are movable and such that a distance therebetween is adjustable. The structure of the first and second mirrors can be suitably modified so long as the distance between the mirrors is adjustable and the sample is sandwiched between the first and second mirrors. The adjusting means need not be a rail/support structure but can alternatively be a rack and gear mechanism, a screw mechanism or the like. Hence, while in the embodiment of FIG. 1a the second mirror 7b shown in front of the sample is mechanically aligned by the adjusting mechanism or the like to achieve parallelism (and to adjust the distance between the mirrors to vary the number of interactions of the reflected light beam with the molecules on the wafer surface), it is evident to one of ordinary skill in the art that the first mirror in the holder member 6 may additionally or alternatively be made adjustable.

Figure 1C:
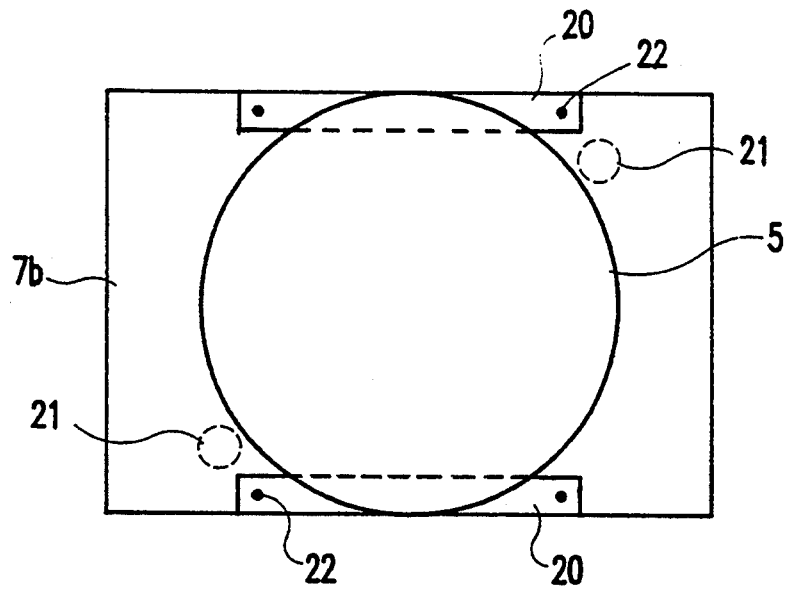
FIG. 1c illustrates a side view of a sample holder with an alignment mechanism.
Figure 1D:
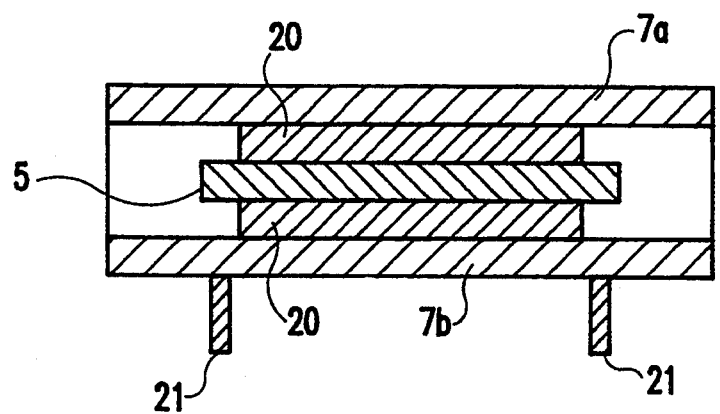
FIG. 1d is a sectional view of the sample holder of FIG. 1c.

As another alternative, as shown in FIGS. 1c and 1d the sample 5 is compressed between both mirrors 7a, 7b by means of spring-loaded screws with highly parallel spacer bars 20 (e.g., preferably formed of PTFE ("Teflon") or the like) between the sample 5 and each mirror. Adjustment knobs 21 may be provided, for example, as shown in FIGS. 1c, and 1d for adjusting the orientation and positioning of the entire assembly system (e.g., mirrors, spacers and sample). Adjustment knobs 21 are preferably diagonal to one another and are rotatable. Knobs 21 may be a cam-like mechanism or the like and operate by being rotated to adjust (e.g., raising or lowering a desired end or ends of the holder assembly) the positioning of the assembly by movably contacting a desired one of the mirrors 7a, 7b (e.g., in FIGS. 1c and 1d, mirror 7b is shown for exemplary purposes) to tilt the assembly. Spring-loaded screws 22 are provided for securing the spacer bars and compressing the sample therebetween.

Thus, as mentioned above, an important feature of the invention is a means for maintaining the parallelism of the mirrors and sample surface to one another, therefore to minimize the loss of transmitted light intensity due to reflections at the wafer surfaces since the Brewster angle can be maintained thereby.

Figure 2:
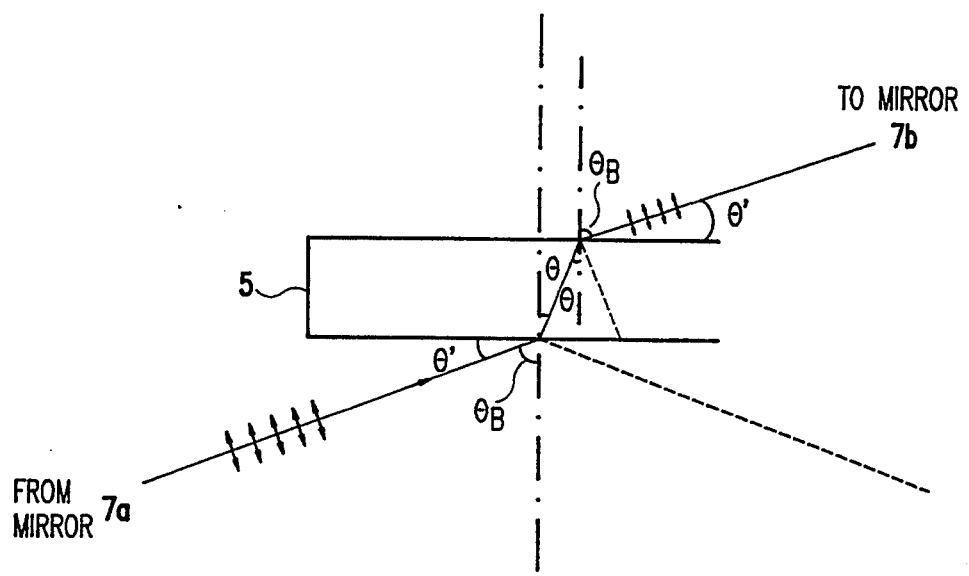
FIG. 2 illustrates a sectional view of the sample being measured and a light beam being refracted therethrough.

The angle of incidence between the collimated p-polarized beam and the normal to the wafer surface is preferably adjustably set and maintained at the Brewster angle. The Brewster angle is determined in a well-known manner and is based on Brewster's law which relates the Brewster angle ($\theta_B$) to the refractive index (n) of the medium for a particular wavelength (e.g., tan $\theta = n$). Generally, $\theta_B + \theta' = 90$ degrees, as shown in FIG. 2. For example, for silicon the Brewster angle $\theta_B$ is 73.7 degrees at room temperature. The importance of maintaining the Brewster angle (and the parallelism of the sample surface and the first and second reflecting mirrors) is that noise due to interference in the reflected and transmitted beam from the silicon surfaces is minimized, if not entirely eliminated. The use of multiple interactions of the excitation light with the surface of the sample accumulates a large signal as compared to noise and thus a high signal-to-noise ratio can be obtained in real-time. Conventional single pass mechanisms fail to accumulate enough signal in a given duration and thus have a poor signal-to-noise ratio unusable for surface study.

As shown in FIG. 2, the incoming collimated and p-polarized light beam is incident at the Brewster angle on the surface of the sample (e.g., the silicon wafer) and is refracted therethrough and reflected from the mirror multiple times (only one time being illustrated in FIG. 2) such that the exit angle is also at the Brewster angle with respect to the normal of the sample surface, thereby preventing or minimizing noise due to interference with the multiple reflections of the light beam at the sample's surfaces. There should be no external and internal reflections at the sample's surface as a result of the collimated p-polarized beam being incident on the surface at the Brewster angle with respect to the normal of the surface of the sample.

The beam having been passing multiple times through the surface of the sample is in turn exited to a detector 9. The beam can be transmitted directly to the detector 9 or by one or more reflecting mirrors 4 positioned in the optical path between the sample and the detector 9 (or by the optical fiber as shown in FIG. 1b and as mentioned above). The detector is typically a portion of an FTIR spectrometer. The choice of the detector varies with the specific wavelength range and time response required. For example, for the Si-H vibration, the preferred detector may be a liquid-N-cooled, InSb detector.

The signal from the detector is typically input to a processor 10 such as a microcomputer or the like which processes the dam using a fast Fourier transform to produce a useful FTIR spectrum which can be interpreted to indicate the presence or absence of certain vibrational features associated with the presence of species on the sample surfaces of interest. For example, one such property comprises the presence or absence of a monolayer of material on the wafer. Thus, the monolayer of the surface can be monitored and examined. Additionally, other properties and qualities include the presence of contaminants (e.g., water, OH or the like) may also be determined in real-time with the arrangement of the invention. It is clear that the processor can be coupled to structural elements (e.g., light source, modulated light beam, collimators, polarizer, mirrors, holder member, etc.) of the invention and can be used as a controller to fully automate the system.

Thus, in the invention, the incident excitation light beam employed is recollimatted with only the p-polarized light component selected. The angle of incidence between the well-collimated p-polarized beam and the wafer surface normal must be set at the Brewster angle (e.g., as designated in FIG. 1 a as $\theta_B$).

As mentioned above, the apparatus of the invention can be used in conjunction with standard FTIR spectrometers, and the apparatus can be suitably scaled to accommodate wafers of various dimensions (e.g., upwards of 8 inches in diameter).

Thus, the invention advantageously utilizes multiple external transmission/reflection of a beam to measure surface species (e.g., at the monolayer level) of a sample (e.g., silicon wafer) which is transparent to light at a given spectral region.

In operation, as shown in FIG. 1a, an excitation light beam is provided from a modulated light source 1 (e.g., an IR light source). The excitation light beam is collimated by one or more collimating means 2 and the collimated light is p-polarized by a polarizer 3. The p-polarized collimated light is directed (either through reflecting means or directly) incident upon a sample 5 at the Brewster angle with respect to the normal of the surface of the sample 5 (e.g., a semiconductor wafer) which is positioned between first and second highly reflective surfaces (e.g., reflecting mirrors) which are in a parallel relationship. The sample 5 is positioned (e.g., sandwiched) between the first and second reflective surfaces and parallel thereto.

The incident angle is at a Brewster angle with respect to the normal of the sample surface, and the collimated p-polarized light is externally transmitted through the sample, beginning at a position adjacent to a first end e.g., first location) thereof, and reflected by the first and second external reflective surfaces a plurality of times until the beam exits the sample at a second position (e.g., at a second end of the sample) of the sample. The number of times that the beam interacts with the sample depends upon the spacing between the first and second external reflective surfaces. For example, a relatively short distance between the first and second reflective surfaces will result in a relatively large number of reflections. Conversely, a large distance between the first and second reflective surfaces will result in a relatively small number of reflections. A typical distance between the first and second reflective surfaces is two millimeters plus the sample thickness. In one embodiment as discussed above with regard to FIGS. 1c and 1d, the spacing between the sample and the first and second reflective surfaces is controlled by the thickness of the replaceable spacer(s) (e.g., Teflon sheet).

The beam exiting from the sample is detected by a detector 9 (e.g., a photodetector as described above) in a known manner and converted into an electrical (analog) signal by suitable means (e.g., means for photoelectrically converting the light intensity received by detector 9 into an electrical signal representing the intensity of the light received by detector 9) known in the art.

The resulting electrical signal may then be converted to a digital signal by means of an analog-to-digital converter (not illustrated) or the like. The resulting digital signal can then be demodulated through Fourier Transformation and be analyzed by a processor/controller 10 (e.g., as shown in FIGS. 1a–1b) utilizing suitable data analysis program(s) (off-the-shelf or customized programs developed by the operator, to determine a surface condition (e.g., a condition of a monolayer) or a property of the sample surface. As mentioned above, such data analysis program(s) are believed to be well within the skill of one of ordinary skill in the art, if not available off-the-shelf. The detector 9 and other elements of the system are suitably controlled by the processor/controller 10. Further, the processor/controller 10 can be coupled to structural elements 10' (e.g., wafer processing control elements etc.), as shown in FIGS. 1a–1b and can be used as a controller to fully automate the system within the processing stream of the sample.

Figure 3:
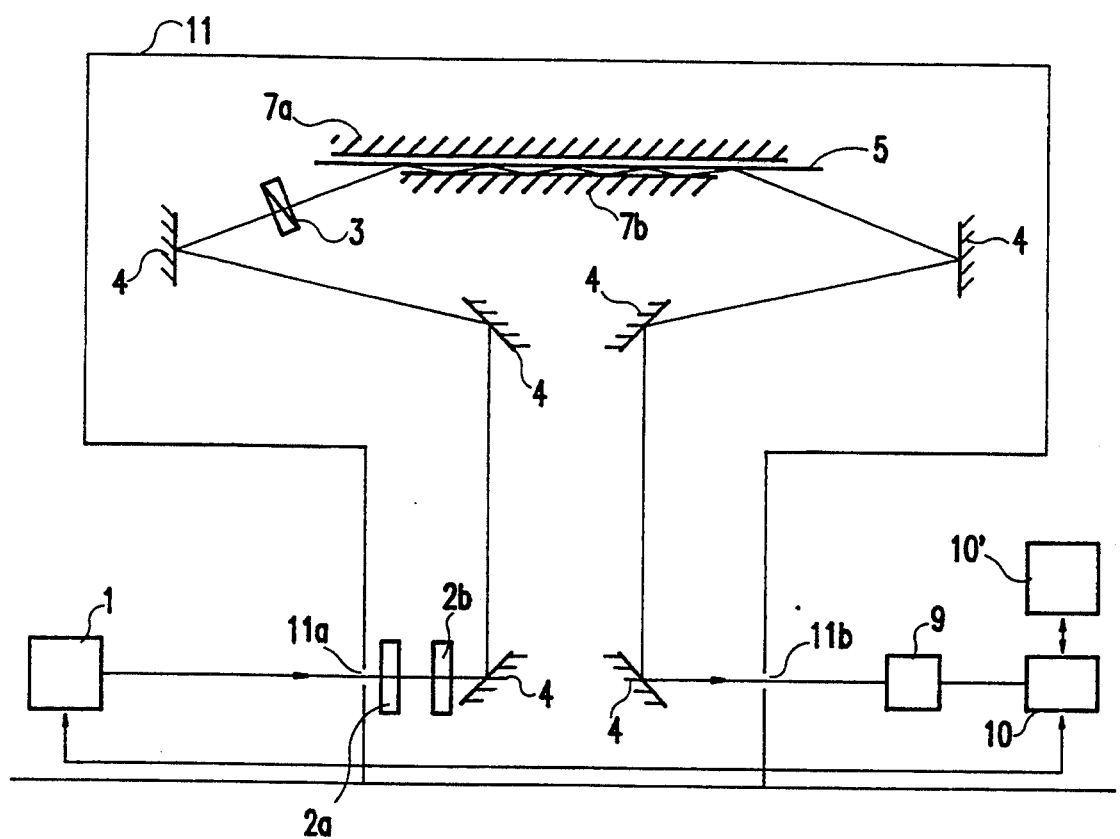
FIG. 3 is a view of another detection system according to the invention.

A second embodiment of the invention is illustrated in FIG. 3 in which a housing 11 is utilized to house most of the structural elements of the invention, with the exception of the light source and detector. Housing advantageously provides a controlled environment, resulting in less chance of contamination and the like. Housing 11 further provides for positioning of the light source and the detector outside the housing, which allows increased versatility of the system in terms of making the light source and detector more easily modifiable or interchangeable. The main use of providing a housing is to allow purging of the system by infrared inactive and inert species (e.g., pure Ar or nitrogen), thereby removing spectral features due to air (especially $H_2O$ and $CO_2$) which often mask the important surface features of interest. Further, the second embodiment utilizes a larger plurality of mirrors to reflect and direct the beam to and from the sample held between the first and second highly reflective surfaces.

In FIG. 3, an excitation light beam is provided from a modulated light source 1 and passes through a window 11a formed in a sealed housing 11. The light beam is preferably collimated by one or more beam collimating means (e.g., 2a, 2b) positioned in the housing 11. The beam collimating means includes one or more collimating lenses such as biconvex lenses or the like.

The collimated light beam is directed and transmitted to a linear polarizer 3 by reflecting means 4 (e.g., one or a plurality of mirrors). Three mirrors 4 are shown in FIG. 3 for directing the collimated beam to the polarizer 3. Similarly to the system of FIG. 1a, the light source for producing tile excitation light beam, the beam collimating means, and the linear polarizer can be easily integrated into a single structure so long as a light beam which is collimated and p-polarized is produced.

The p-polarized light is transmitted through the polarizer ideally located just before incidence on the sample to best achieve and maintain the desired and critical polarization state. As mentioned above, the use of mirrors is advantageous in reducing the amount of space required by the apparatus in that the positioning of the optical path of the light beam can be suitably folded to fit space requirements.

The p-polarized light is passed through the linear polarizer 3 to the surface of a sample 5. Alternatively, the excitation beam may be collimated, p-polarized and transmitted directly to the sample 5, without the use of any intermediate reflecting means, collimation means and polarizer. Further, optical fibers can be advantageously used as discussed above.

The sample 5 is adjustably held by a holder member (not shown in FIG. 3) between first and second highly reflective surfaces so as to be sandwiched therebetween in a manner similar to the first embodiment shown in FIG. 1a. The first and second highly reflective surfaces may comprise mirrors or the like. The mirrors may comprise the same materials as the reflecting means 4. The holder member is used to maintain the Brewster angle and parallelism between the first and second mirrors and the sample surface.

A plurality of mirrors (e.g., first and second mirrors 7a, 7b) are provided to ensure reflection and transmission of the p-polarized collimated light beam through the sample 5. Either or both of the first mirrors 7a, 7b may be adjustable by suitable adjusting means (e.g., a support member on movable rails, a rack and gear mechanism, a screw mechanism or the like) which moves the highly reflective surface(s) (e.g., mirror(s) 7a, 7b) in a direction normal to a surface of the sample being investigated, and which adjusts a distance between the first and second mirrors.

Thus, the mirror(s) may be mechanically aligned by the adjusting mechanism or the like to achieve parallelism (and to adjust the distance between the mirrors to vary the number of interactions of the reflected light beam with the molecules on the wafer surface/surfaces).

Similarly to the first embodiment, an important feature of the second embodiment of the invention is that at least one of the mirrors is adjustable so that the parallelism of the mirrors and sample surface can be maintained and so that the angle of incidence between the collimated p-polarized beam and the normal to the wafer surface is set and maintained at the Brewster angle. Maintaining the Brewster angle and the parallelism of the sample surface and the first and second reflecting mirrors 7a, 7b minimizes noise and interference in the reflected and transmitted beam and this allows a high signal-to-noise ratio to be obtained in real-time.

The beam having been passed multiple times through the sample surface is in turn reflected to a detector 9 via one or more reflecting means 4 (e.g., mirrors). Three mirrors 4 are shown in FIG. 3 for directing the beam to The detector 9 after the beam has finished its multiple transmissions through the sample. Of course, as mentioned above with regard to the first embodiment, the beam can be reflected directly to detector 9 from the distal end of the sample (e.g., the exit position of the beam from the sample). The detector is positioned outside of the housing 11 similarly to the light source 1 for producing the excitation light beam and receives the beam through a window 11b formed in the housing 11. The detector 9 may be coupled to a processor similarly to the first embodiment, to control the overall system and to analyze the properties and quality of the surface of the sample based on the output of the detector. Based upon the output of the detector, the Brewster angle can be found and maintained by adjusting the mirrors having the sample therebetween and by ensuring that the mirrors and sample surface are parallel. Further, the processor 10 can be coupled to one or more structural elements 10' (e.g., wafer processing control elements etc.), as shown in FIG. 3, and can be used as a controller to fully automate the system within the processing stream of the sample.

With the arrangement of the invention, the surface species of the sample that are, for example, IR active, can be detected automatically, reliably, and in real-time, by irradiating the p-polarized light at the Brewster angle, and determining whether the exit light has certain prescribed features. Further, conventional silicon wafers or the like can be reliably investigated without the need for any special preparations and the time to investigate the object of interest (e.g., the wafer) takes much less time than the conventional methods. Accordingly, sample processing can be terminated or adjusted in real-time based on results of the FTIR spectrum obtained by multiple interactions between the sample surfaces and the excitation light beam in real-time. More specifically, the entire wafer processing system which includes the FTIR system can be advantageously computer-controlled and automated with immediate feedback of the analysis of the surface which provides monolayer sensitivity and real-time capabilities. As such, the invention can be used in a plurality of wafer processing steps such as etching or the like and progress in a processing step can be monitored in real-time such that the next step in the processing cycle can be automatically begun.

Additionally, the system and method of the invention is non-destructive and, as mentioned above, there is no need for special sample preparation.

While the invention has been described in terms of a single preferred embodiment, those skilled in the art will recognize that the invention can be practiced with modification within the spirit and scope of the appended claims. For example, while the invention has been shown and described in the second embodiment as being implemented in a substantially sealed housing, it will be understood by those skilled in the art that the invention can be used wherever in situ analysis of surfaces of a sample is required. Thus, a sealed environment is not required and thus the structure and method of the invention are extremely versatile. As another example, the means to direct the beam from the source to the sample and from the sample to the detector can be accomplished by the use of optical fibers which preserve the polarization, collimation, and light intensity.

Having thus described our invention, what we claim as new and desire to secure by Letters Patent is as follows:

1. An apparatus for measuring a condition of a sample, comprising:
a light source for emitting a light beam;
means for collimating said light beam from said light source to produce a collimated light beam;
means for p-polarizing said collimated light beam to form a p-polarized light beam;
means for directing said p-polarized light beam to a surface of the sample such that an angle of incidence of said p-polarized light beam to a normal of the surface is at a Brewster angle;
first and second reflecting means between which the sample is positioned for reflecting said p-polarized light beam through the surface of the sample a plurality of times;
means for adjusting a distance between said first and second reflecting means to adjust a number of interactions of said p-polarized light beam with the surface of the sample; and
means for detecting said light beam having been output from the surface of the sample.

2. The apparatus according to claim 1, wherein said means for adjusting includes means for adjusting an orientation of at least one of said first reflecting means, said second reflecting means and the surface of the sample such that first reflecting means, said second reflecting means and the surface of the sample are parallel to one another.

3. The apparatus according to claim 2, wherein said means for adjusting an orientation includes means for adjusting at least one portion of said at least one of said first reflecting means, said second reflecting means and the sample relative to other portions of said at least one of said first reflecting means, said second reflecting means and the sample.

4. The apparatus according to claim 1, further comprising means for aligning the sample between said first and second reflecting means, said aligning means comprising at least one spacer having a predetermined thickness and being positioned on at least one of said first and second reflecting means such that the sample is separated from said at least one of said first and second reflecting means by said predetermined thickness and such that parallelism is maintained between said first and second reflecting means and the sample.

5. The apparatus according to claim 1, wherein said means for directing includes means for directing said p-polarized light beam at a first position of the surface of the sample.

6. The apparatus according to claim 5, wherein said p-polarized light beam having been reflected said plurality of times exits the surface at a second position of the surface and is reflected by one of said first and second reflecting means to said detecting means.

7. The apparatus according to claim 1, further comprising means for analyzing said collimated light beam received by said detecting means to determine the condition of the sample.

8. The apparatus according to claim 7, wherein said means for collimating includes a collimating lens.

9. The apparatus according to claim 8, wherein said means for p-polarizing comprises a linear polarizer.

10. The apparatus according to claim 9, wherein said detecting means comprises an infrared spectrometer.

11. The apparatus according to claim 1, wherein said first and second reflecting means comprise first and second mirrors, respectively.

12. The apparatus according to claim 1, wherein said means for directing the collimated beam to said p-polarizing means adjacent to the sample and then to said means for detecting, comprises an optical fiber.

13. An apparatus according to claim 1, further comprising means for holding the sample between said first and second reflecting means, said holding means comprising a vacuum chuck.

14. The apparatus according to claim 1, further including means for providing closed-loop control of said light source, said means for collimating, said means for p-polarizing, said means for directing, said first and second reflecting means, said means for adjusting and said means for detecting.

15. An apparatus for real-time detection of a property of an object, said apparatus comprising:
   means for producing modulated and collimated p-polarized light;
   a plurality of reflective surfaces for receiving and directing the collimated p-polarized light, first and second reflective surfaces of said plurality of reflective surfaces being opposed to and parallel to one another and having an adjustable relation therebetween, the object being interposed between said first arid second reflective surfaces;
   means for maintaining said first reflective surface, said second reflective surface and a surface of the object parallel to one another, wherein said collimated p-polarized light is externally transmitted through the object, beginning at a first location, and reflected by said first and second reflective surfaces a plurality of times until said collimated p-polarized light beam exits the object at a second location thereof, wherein said collimated p-polarized light is directed incident upon the object at an incident angle with respect to a normal of the surface of the object, said incident angle being a Brewster angle;
   means for adjusting a distance between said first and second reflective surfaces, wherein a number of times said p-polarized light beam is reflected is dependent upon said distance between said first and second reflective surfaces; and
   means for analyzing said collimated p-polarized light beam having exited the object to determine the property of the object.

16. An apparatus according to claim 15, further comprising means for holding the object between said first and second reflective surfaces, said holding means comprising a vacuum chuck.

17. The apparatus according to claim 15, wherein said means for analyzing includes means for demodulating said collimated p-polarized light beam having exited the object.

18. A method of adjusting an angle of a sample held between first and second reflecting means, comprising the steps of:
   sandwiching the sample between said first and second reflecting means such that a light beam directed incident upon the sample at an incident angle with respect to a normal of a surface of the sample is at a Brewster angle; and
   adjusting the incident angle of the sample by rotating the sample.

19. A method for real-time detection of a property of an object, said method comprising the steps of:
   a) producing modulated and collimated p-polarized excitation light;
   b) providing a plurality of reflective surfaces, first and second reflective surfaces of said plurality of reflective surfaces being opposed to one another and having an adjustable distance therebetween;
   c) providing an object to be monitored between said first and second reflective surfaces;
   d) maintaining a surface of the object, said first reflective surface and said second reflective surface parallel to one another;
   e) directing said collimated p-polarized excitation light to said first and second reflective surfaces such that said first and second reflective surfaces receive and direct the collimated p-polarized light incident upon the object at an incident angle with respect to a normal to the surface of the object, said incident angle being a Brewster angle, said collimated p-polarized light being transmitted through the object and reflected by said first and second reflective surfaces a plurality of times until said collimated p-polarized light beam exits the object; and
   f) analyzing said collimated p-polarized light beam having exited the object to determine the property of the object.

20. The method according to claim 19, wherein said step of directing includes externally transmitting said collimated p-polarized light through the object, beginning at a first location thereof, and reflecting said collimated p-polarized light by said first and second reflective surfaces a plurality of times until said collimated p-polarized light beam exits the object at a second location thereof.

21. The method according to claim 20, further comprising a step of adjustably maintaining a distance between said first and second reflective surfaces, wherein a number of times said p-polarized light beam is reflected is dependent upon the distance between said first and second reflective surfaces.

22. The method according to claim 19, wherein said step of analyzing includes a step of determining a presence of a layer at a monolayer level on the surface of the object based on features detected on the surface of the object.

23. The method according to claim 19, wherein said method further includes a step of providing closed-loop control of said steps (a)-(f).

* * * * *